United States Patent [19]
Leiner et al.

[11] Patent Number: 6,037,178
[45] Date of Patent: Mar. 14, 2000

[54] METHOD FOR QUALITY CONTROL OF AN ANALYZING SYSTEM

[75] Inventors: Marco Jean-Pierre Leiner, Grax, Austria; James K. Tusa, Alpharetta, Ga.

[73] Assignee: AVL Medical Instruments AG, Schaffhausen, Switzerland

[21] Appl. No.: 08/678,101

[22] Filed: Jul. 11, 1996

[30] Foreign Application Priority Data

Jul. 17, 1995 [AT] Austria .................................... 1215/95

[51] Int. Cl.⁷ .......................... G01N 33/00; G01N 33/48
[52] U.S. Cl. ............................. 436/50; 422/68.1
[58] Field of Search ..................... 436/50, 465; 422/68.1

[56] References Cited

U.S. PATENT DOCUMENTS

| | | | |
|---|---|---|---|
| 5,080,865 | 1/1992 | Leiner et al. | 422/68.1 |
| 5,228,350 | 7/1993 | Karpf et al. | 73/864.81 |
| 5,288,646 | 2/1994 | Lundsgaard et al. | 436/165 |
| 5,351,563 | 10/1994 | Karpf et al. | 73/864.84 |
| 5,405,510 | 4/1995 | Betts et al. | 204/153.1 |

FOREIGN PATENT DOCUMENTS 0226593  1/1992  European Pat. Off. .

OTHER PUBLICATIONS

International Pat. Pub. WO 92 01928 to S. Cozzette et al. entitled Method for Analytically Utilizing Microfabricated Sensors During Wet–Up, dated Feb. 6, 1992.

International Pat. Pub. WO 85/04719 to R. Baker et al. entitled "Self–Calibrating Single–Use Sensing Device for Clinical Chemistry Analyzer," dated Oct. 24, 1985.

*Primary Examiner*—Lila Feisee
*Assistant Examiner*—Michael Pak
*Attorney, Agent, or Firm*—Watson Cole Grindle Watson, P.L.L.C.

[57] ABSTRACT

Quality control of an analyzing system that includes a portable analyzer with insertable single-use cartridges whose sample chamber contains optical and/or electro-chemical sensors is accomplished by bringing the sensors in the single-use cartridge into contact, or are in contact with, a calibrating and/or conditioning medium, the calibrating and/or conditioning medium exhibiting chemical and/or physical parameters which influence the characteristic of at least one of the sensors. Just before a sample is measured, the sensors are contacted with a quality control liquid which is identical with the calibrating and/or conditioning medium within a predetermined desired range of accuracy for the sample components to be measured, as regards the chemical and/or physical parameters influencing the characteristic of at least one sensor during calibration and/or conditioning. The instantaneous control values obtained on the basis of the calibration values are subsequently compared to known target control values.

12 Claims, 2 Drawing Sheets

METHOD FOR QUALITY CONTROL OF AN ANALYZING SYSTEM

BACKGROUND OF THE INVENTION

The present invention relates to a method for quality control of an analyzing system that makes use of a portable analyzer with insertable single-use cartridges whose sample chamber contains optical and/or electrochemical sensors, in particular sensors which are designed for determining clinically relevant parameters (pH, $pCO_2$, $pO_2$), ions (e.g., $Li^+$, $Na^+$, $K^+$, $Mg^{++}$, $Ca^{++}$, $Cl^-$), and enzyme substrates (e.g., glucose, lactate, urea) in biological fluids.

Following is a definition of some major technical terms of the invention in order to facilitate comprehension.

Analyzer: Measuring instrument based on optical and/or electrochemical sensors for measurement of samples (blood samples, for instance).

Portable analyzer: Point-of-care measuring instrument based on optical and/or electrochemical sensors. The sensors are incorporated in single-use cartridges which are inserted into the analyzer for sample measurement and discarded after the measuring process.

Sensor: Optical or electrochemical measuring element determining the concentration or partial pressure of at least one chemical component dissolved in a fluid. Several sensors may be used for simultaneous determination of the concentrations or partial pressures of different chemical components.

Simultaneous measurement: The sensors of a sensor bank are contacted with the medium to be measured (calibrating medium, control liquid, sample) during one and the same step of the process. Detection of the measuring signals need not take place simultaneously.

Single-use cartridge: A part which may be brought into contact with a portable analyzer by mechanical as well as electrical and/or optical means, featuring at least one sample chamber and sensors that are in at least indirect contact with this chamber. The single-use cartridge is designed for measurement of a single sample.

Conditioning: Temporary contact of the sensors with a given medium in order to obtain a stable sensor characteristic. Upon contact with aqueous or moist gaseous media, dry-stored sensors exhibit a characteristic that is changing over time. A similar effect is produced, in particular with sensors based on ion-permeable materials, by the diffusion-induced exchange of chemical components with aqueous media of different composition.

Sensor characteristic: Functional relationship between the concentration (or partial pressure) of a chemical component contained in an aqueous solution (independent variable) and the magnitude of a measurable optical or electrical signal of an optical or electrochemical sensor.

Calibration: Determination of the sensor characteristic.

One-point calibration: Calibration at an expected value of the quantity to be measured. For the purpose of calibration the signal must usually be obtained at two or more values of the quantity to be measured. If the functional relationship described by the characteristic is at least partially known, however, as in the instance of batchwise determination during manufacture or reproducible manufacturing, it will usually suffice to obtain the signal at a single value of the quantity to be measured in order to obtain complete calibration.

Calibrating medium, calibrating liquid: Aqueous solution or gaseous mixture containing at least one chemical component to be determined by means of a sensor bank, the concentration or gas partial pressure of this component being known and corresponding to an expected value of the respective chemical component(s) in the given measuring situation.

Quality control: Simultaneous determination of the concentrations of dissolved chemical substances and/or gas partial pressures of a quality control liquid by means of a sensor bank (for example, a single-use cartridge), and subsequent comparison of instantaneous and target values.

Quality control liquid: Aqueous solution supplied in a container (preferably made of glass) preferably impermeable to gases (such as $O_2$, $CO_2$, $N_2$), water, and chemical substances that are soluble in aqueous systems, which is treated with a gas of known composition and contains various chemical components of a liquid specimen to be measured by means of a sensor bank, the concentration of these components corresponding to an expected value of the measurement variable in the given measuring situation.

Specimen: Fluids (for example, biological fluids, such as whole blood, serum, urine). Concentrations or gas partial pressures of the components to be determined are essentially unknown.

Sample: Random sample of the specimen.

Sample measurement: Simultaneous determination of the concentrations and/or gas partial pressures of the chemical substances dissolved in a sample by means of a sensor bank (such as a single-use cartridge).

In clinical laboratories various analyzers are used for in-vitro analyses of biological fluids (blood, urine, plasma, serum). The instruments mostly are based on electrochemical sensors which are calibrated at one or more expected values of the quantities to be measured, by means of liquid and gaseous calibrating media provided in the instrument, before the actual measuring process takes place. For calibration of the individual sensors, various liquid and gaseous calibrating media are employed.

It is often necessary to check accuracy and reliability of such measuring systems by means of quality control liquids. These liquids are aqueous, saline, pH-buffered solutions treated with a gas of known composition of $O_2$ and $CO_2$ and supplied in sealed glass containers. These liquids may contain various additives to increase gas solubility, tensides to increase wettability, and biocides to prevent biological activities. Quality control liquids preferably are used for simultaneous control of all sensors contained in the instrument; their chemical composition is distinct from that of the calibrating media used.

DESCRIPTION OF THE PRIOR ART

In contrast to the stationary analyzing equipment used in large clinical laboratories, a number of portable analyzers (point of care instruments) have become known (see EP 0 460 343 B1, U.S. Pat. No. 5,080,865, WO92/01928, U.S. Pat. No. 5,288,646). They are based on optical or electrochemical sensors incorporated in disposable cartridges. Since a new cartridge is used for each analysis, the requirements to be met by the sensors differ from those of the stationary equipment. As only a single calibrating medium is used, the sensor characteristics must be determined at least partly during the manufacturing process, or must be otherwise known. The characteristic data are fed into the analyzer prior to each cartridge measurement, or they are stored in the analyzer. Due to the cost-saving use of a single calibrating medium, calibration takes place at a single expected value of the respective variable (one-point calibration), simultaneously for all sensors contained in the cartridge. As soon as a single-use cartridge has been inserted into the portable analyzer, all sensors should be ready for use without further conditioning measures.

Although conventional quality control liquids may be used with disposable cartridges, the sensors cannot be employed for subsequent sample measurement due to the diffusion-induced exchange between chemical components of such control liquids and the sensors, or rather, additional steps and measures are required in such instances, which would lead to further expense.

Since there is a slow, diffusion-induced exchange of chemical substances between the sensor materials (usually supplied as layer structures) and the measuring media (calibrating medium, control medium, sample), the chemical composition of the sensitive layers will change. Due to changes in concentration, the sensor characteristics will drift. Depending on the chemical composition, duration of exposure and temperature of the media in contact with the sensors, different measured results will be obtained, depending on whether the specimen is measured after calibration or after control measurement. As a consequence, known types of quality control liquids or methods of quality control will be useful in checking the reliability and accuracy of the analyzer, but not the reliability and accuracy of a single-use cartridge and sensors designed for measurement of the specimen.

In EP 0 226 593 B, for example, an analyzing system for measuring blood samples is disclosed, in which a disposable cartridge is provided. The cartridge comprises a first gas-impermeable container for a calibrating solution A, and a second such container for a calibrating solution B, the chemical characteristics of the two calibrating solutions being distinct but known. The two calibrating solutions serve for two-point calibration of the cartridge. No provisions are made for quality control as defined above.

A self-calibrating single-use cartridge for a clinical analyzer is described in WO 85/04719. The cartridge has a rotatable reservoir with several chambers, one of which contains a calibrating liquid and the other one a sample. By rotation of the reservoir the individual chambers are connected to the actual measuring channel one after the other, where the desired parameters for the calibrating liquid and the sample are determined and subsequently evaluated.

SUMMARY OF THE INVENTION

It is an object of the present invention to propose methods of quality control and quality control liquids which will permit first a control measurement and then measurement of a specimen by means of one and the same single-use cartridge, in addition to providing information on the reliability of the analyzer, or rather, reliability and accuracy of the individual sensors contained in the single-use cartridge.

In the invention this object is achieved by providing that the sensors in the single-use cartridge are brought into contact, or already be in contact with, a calibrating and/or conditioning medium, the calibrating and/or conditioning medium exhibiting chemical and/or physical parameters which influence the characteristic of at least one of the sensors, and contacting the sensors with a quality control liquid just before a sample is measured, which quality control liquid is identical with the calibrating and/or conditioning medium within the desired range of accuracy for the sample components to be measured, as regards those chemical and/or physical parameters influencing the characteristic of at least one sensor during calibration and/or conditioning, and further comprising the instantaneous control values obtained on the basis of the calibration values with the known target control values.

The object of the invention is further achieved by providing that the sensors in the single-use cartridge be brought into contact, or already be in contact, with a calibrating and/or conditioning medium, and that the sensors be contacted prior to sample measurement with a quality control liquid whose $CO_2$/pH equilibrium curve and $pH_2O$ in the interesting measuring range and at a given measuring temperature be identical with the respective values of the calibrating and/or conditioning medium within the desired range of accuracy for the sample components to be measured.

It will be an advantage if the ionic strength of the quality control liquid is identical with that of the calibrating and/or conditioning medium in the interesting measuring range and at a given pH, within the desired range of accuracy for the sample components to be measured, or if the osmotic pressure of the quality control liquid is identical with that of the calibrating medium and/or conditioning medium.

A quality control liquid of the invention is characterized by its being identical with the calibrating and/or conditioning medium within the desired range of accuracy for the sample components to be measured, as regards those chemical or physical parameters which influence the characteristic of the individual sensors during a preceding calibrating or conditioning process.

The single-use cartridges may be equipped with any combination of the sensors described below, permitting use of both the method and quality control liquid of the invention.

pH Sensors

Optical sensors for determination of the pH value usually contain a pH indicator, such as an organic acid or base, which is immobilized in an ion-permeable, mostly hydrophilic polymer layer by covalent, electrostatic, or adsorptive bonds. By ionic exchange (e.g., $H^+$, or $OH^-$) via ion-permeable materials the immobilized pH indicators may be brought into at least indirect contact with a sample (M. J. P. Leiner and O. S. Wolfbeis, "Fiber Optic pH-Sensors", in O. S. Wolfbeis, "Fiber Optic Chemical Sensors and Biosensors", CRC-Press, Boca Raton, 1991, Chapter 8). In dependence of the pH value of the specimen (pH=−log $(aH^+)$) a thermodynamic equilibrium is established between protonated and deprotonated forms of the pH indicator. From the concentration ratio of the two forms, which is measured by optical methods, the pH value of the specimen may be inferred.

Suitable electrochemical sensors for determination of pH are glass electrodes, liquid membrane electrodes, antimony electrodes, field effect transistors (ISFET), solid state systems (noble metal/noble metal oxide systems, such as $Ir/IrO_2$, and $Pd/PdO_2$), and redox systems.

$CO_2$ Sensors

Optical sensors for determination of the $CO_2$ partial pressure of a liquid specimen usually consist of a reaction chamber built in layers and an ion-impermeable, gas-permeable material separating the reaction chamber from the specimen. The reaction chamber is frequently identical with the indicator-carrying material of an optical pH sensor. The reaction chamber further contains one or more pH buffering agents, such as carbonates, phosphates, and/or organic compounds featuring acid or basic reactions in aqueous media. At a given temperature, water content and composition of the buffering agents, the pH value of the reaction chamber exhibits a characteristic dependence on $pCO_2$ of the specimen.

Electrochemical sensors for determination of the $CO_2$ partial pressure often exhibit a layer structure essentially similar to that of optical sensors. Instead of an optical pH indicator one of the pH sensitive electrodes described above is employed for pH measurement of the reaction chamber.

Since gas-permeable, ion-impermeable separating materials are also permeable to water by isothermal distillation, an exchange of water will take place between specimen chamber and reaction chamber, in addition to the gas exchange. Water is picked up or given off if the partial pressure of water vapor or osmotic pressure of the reaction chamber is distinct from that of the medium in the specimen chamber. The exchange process will enter into a state of equilibrium only when the partial pressure of water vapor and/or osmotic pressure of both chambers have assumed the same value.

$O_2$ Sensors

Optical sensors for determination of the $O_2$ partial pressure of a liquid or gaseous specimen usually contain an optical $O_2$ indicator which is immobilized in a preferably ion-impermeable polymer layer by covalent, electrostatic, or adsorptive bonds. To avoid optical interferences with the specimen, a second polymer layer, which is filled with pigments and preferably is ion-impermeable, often is used for the purpose of optical decoupling of the specimen chamber from the polymer layer carrying the indicator.

Electrochemical sensors for determination of the $O_2$ partial pressure of a liquid or gaseous specimen usually are amperometric electrodes. The actual electrode arrangement is frequently separated from the specimen chamber by an ion-impermeable, gas-permeable separating material.

Ion Sensors

The relevant scientific literature describes various optical recognition systems of various design for determination of the concentrations (or activities) of inorganic cations or anions ($NH_4^+$, $Li^+$, $K^+$, $Na^+$, $Mg^{++}$, $Ca^{++}$, $Cl^-$). Depending on the recognition system the chemical components are provided in ion-permeable polymer materials often configured as layer structures.

Electrochemical sensors for determination of the concentrations or activities of the inorganic cations or anions referred to above usually are potentiometric measuring systems. The recognition system is based on an ionophor which is physically dissolved in a polymer material.

Substrate Sensors

Optical and electrochemical sensors for the purpose of determining the concentrations of biological substances reacting with enzymes, such as glucose, lactate, urea, which are described in the relevant scientific literature, are based on recognition systems which usually undergo a specific biochemical reaction with the substance to be determined (substrate). Parallel to the enzymatic substrate decomposition other substances, such as $O_2$, $H_2O_2$, $NH_4^+$, $H^+$ are consumed and/or formed. The latter may be determined by means of the sensors described above.

To determine glucose concentration, for instance, an optical or electrochemical $O_2$ sensor is employed, which contains an enzyme in addition to the other components (see above). By means of $O_2$ measurement it is possible to determine glucose concentration in the specimen.

Reference Electrodes

Unlike optical sensors electrochemical measuring devices require a reference element. In potentiometric electrodes the reference electrode is often located in the specimen chamber, i.e., at a distance from the actual measuring electrode. In an exemplary variant of the invention the potentiometric reference electrode is a metal electrode (e.g., Ag) which is in indirect contact with the specimen chamber via an ion-permeable material. The ion-permeable material contains the ionic components necessary for the potential-building process (e.g., AgCL/KCl).

A liquid suitable for simultaneous calibration of several sensors in a single-use cartridge contains the ionic and/or gaseous components to be determined at known concentrations and/or partial pressures corresponding to an expected value of the measurement variable in the given measuring situation. A liquid of such composition can also be used for conditioning of the sensors. As the solubilities of the gaseous components ($O_2$, $CO_2$) in aqueous liquids will strongly depend on temperature, and as there is a diffusion-controlled, temperature-dependent gas exchange with the plastic materials of the single-use cartridge, the gas partial pressures of the calibrating liquid are not known with sufficient accuracy at the time of calibration, in particular when the temperature of the single-use cartridge is adjusted from storage temperature (0–35° C.) to measuring temperature (37° C.).

One possibility of obtaining more accurately known gas partial pressures at the time of calibration is the use of a liquid calibrating medium treated with calibrating gas in a separate gas-impermeable container preferably integrated in the single-use cartridge (WO 92/01928).

If the presence of two liquids (conditioning liquid and calibrating liquid) in a single-use cartridge is to be avoided, the sensors in a single-use cartridge must be dry-stored until calibration takes place. By contact with liquid media (calibrating liquid, control liquid, aqueous specimen) dry-stored sensors will slowly absorb water (hydration, wet-up, conditioning). The kinetics of hydration depends on different factors, such as temperature, pH, or physico-chemical material properties. Since the sensor characteristic depends on the state of hydration of the respective sensors, it will vary continuously at a non-uniform rate. WO 92/01928 discloses computer-assisted methods for compensation of such sensor signals varying monotonously with hydration processes.

According to the invention, quality control of dry-stored sensors is possible if the following steps are taken:

Production-inherent characteristics of the individual sensors are read into the analyzer, or are already stored therein, and the cartridge is inserted into the analyzer.

The sensors are subjected to a liquid calibrating medium.

The calibration signals of the sensors are detected simultaneously, taking into account the time lapse between the primary contact of the sensors and the calibrating liquid and the detection of the calibration signals.

The sensors are contacted with a quality control liquid, with the possible addition of a gas of known composition for the purpose of separating the calibrating liquid from the quality control liquid, which latter, as regards those chemical and/or physical parameters that influence the characteristic of at least one sensor during calibration, should be identical with the calibrating liquid within the desired range of accuracy for the sample components to be measured.

The control signals of the sensors are detected, taking into account the time lapse between the primary contact of the sensors and the calibrating liquid and the detection of the control signals.

From the characteristics read into, or known by, the analyzer, and the calibration and control signals detected simultaneously, instantaneous control values are determined for the individual sensors.

The instantaneous control values are compared with the known target control values.

Subsequent to the process of quality control, the same cartridge is employed for sample measurement, if the instantaneous control values are identical with the target control values within the desired range of accuracy.

Gas partial pressures which are known much more accurately at the time of calibration may be obtained by treating the sensors stored in contact with a liquid conditioning medium, with a calibrating gas of known composition that is preferably provided in the portable analyzer. Due to the preceding lengthy contact of the sensors and the conditioning liquid, whose residues remaining in the ion-permeable materials of any pH sensor provided, will supply a calibrating medium for the pH sensor if treated with a $CO_2$-containing calibrating gas, the components exchangeable by diffusion between the sensors and the liquid calibrating medium, are in a state of chemical equilibrium. According to the invention the method for quality control of sensors that are stored in contact with a liquid conditioning medium is characterized by the following steps:

Production-inherent characteristics of the individual sensors are read into the analyzer, or are already stored therein, and the cartridge is inserted into the analyzer.

The conditioning liquid present in the sample chamber is replaced by a gaseous calibrating medium, any residues of the conditioning liquid remaining in the sample chamber or in contact with individual sensors being treated with the calibrating gas.

The calibration signals of the sensors are detected simultaneously.

The calibrating gas is replaced by a quality control liquid, which, as regards those chemical and/or physical parameters that influence the characteristic of at least one sensor during calibration and/or conditioning, should be identical with the calibrating liquid and/or calibrating gas within the desired range of accuracy for the sample components to be measured.

The control signals of the sensors are detected simultaneously.

With the use of the characteristics read into or known by the analyzer and the calibration and control signals detected simultaneously, instantaneous control values are determined for the individual sensors.

The instantaneous control values are compared with the known target control values.

Subsequent to the process of quality control the same cartridge is employed for sample measurement, if the instantaneous control values are identical with the target control values within the desired range of accuracy.

Due to the variable concentrations of the electrolytes exchangeable between calibrating liquid, control liquid, or specimen and a reference electrode, a diffusion potential will arise at the phase interface of potentiometric reference electrodes. If the respective electrolyte concentrations are known in both phases, the diffusion potential may be calculated and its effect on the measured result taken into consideration. With given materials the kinetics of the exchange process will depend on the temperature, the concentration gradients of the electrolytes, and the physical properties of the materials used. At a given time after contact with saline solutions the diffusion potential may be calculated in dependence of temperature and the duration of contact.

As regards the sensors used in this context, it should be noted that low-molecular molecules that are preferably uncharged will slowly diffuse through ion-permeable as well as ion-impermeable sensor materials, and may influence the sensor characteristic of optical and electrochemical sensors by changing the chemical and/or physical material properties and interacting with chemical recognition systems.

Preferably low-molecular, electrically charged molecules (ions) usually will diffuse freely through hydrophilic polymer materials (hydrogels), changing the sensor characteristic of suitably structured sensors (e.g., optical pH sensors, optical ion sensors, optical and electrochemical substrate sensors).

The exchange processes will reach a state of equilibrium only when the chemical potentials of the substances to be exchanged are in balance. Although it is principally possible to compute the sensor characteristic prevailing at a given time from the known duration and temperature of the contact with liquid media, this method is quite inaccurate, especially for sequential contact with fluids of different compositions (calibration liquid, control liquid, specimen). Use of the quality control liquid according to the invention will prevent the above disadvantages.

An ideal quality control liquid for sensors in a single-use cartridge would have the same composition as the calibrating liquid (in substantially dry-stored sensors), or as the residues of the conditioning liquid remaining in the sensor materials (in wet-stored sensors). The demands to be met by a quality control liquid according to the invention will only have to satisfy the criteria laid down in the patent claims, however, as (1) small amounts of certain additives have no significant influence on the measuring properties of the sensors;

(2) in the instance of substrate sensors (e.g., glucose sensors) the calibrating liquid, for example, contains no substrate, whereas the quality control liquid should have a substrate concentration corresponding to the expected value of substrate concentration;

(3) for checking of the ion sensors different relative concentrations of cations ($Na^+$, $K^+$, . . . ) are possible, and only the same total ionic strength is required.

The control liquid according to the invention has the following characteristics:

(1) In the interesting measuring range ($pCO_2$ 10–120 torr, pH 6.8–8.0) and at a given measuring temperature (20–40° C.), the $CO_2$/pH equilibrium curve (pH=f($pCO_2$, T, concentrations of pH buffer components, ionic strength)) (see also "The Acid-Base Status of the Blood, Siggaard-Anderson, Munksgaard, Copenhagen 1974; or "pH-Wert Berechnung", C. Bliefert, Verlag Chemie Weinheim, New York 1978) of the quality control liquid is identical with that of the calibrating liquid or conditioning liquid within the desired range of accuracy (see FIG. 3).

(2) In the instance of optical pH and ion sensors, especially, the ionic strength of the control liquid should be the same as that of the control liquid or conditioning liquid in the interesting measuring range and at given pH.

(3) The quality control liquid may have any convenient pCO2 or/and $pO_2$, for example, in the interesting measuring range. The gas partial pressures Of $pCO_2$ and $pO_2$ may differ from those of the calibrating liquid or the conditioning liquid and the calibrating gas.

Single-use cartridges that are suitable for use with the method of the invention are described in EP 0 460 343 B1 referred to above, for example.

BRIEF DESCRIPTION OF THE DRAWINGS

Furthermore, the variant of a single-use cartridge shown in FIGS. 1 and 2 of the present invention may be used, FIG. 1 giving a view of the cartridge from above, and FIG. 2 a section along line II—II in FIG. 1.

DETAILED DESCRIPTION OF THE PREFERRED EMBODIMENT

Figure 1:
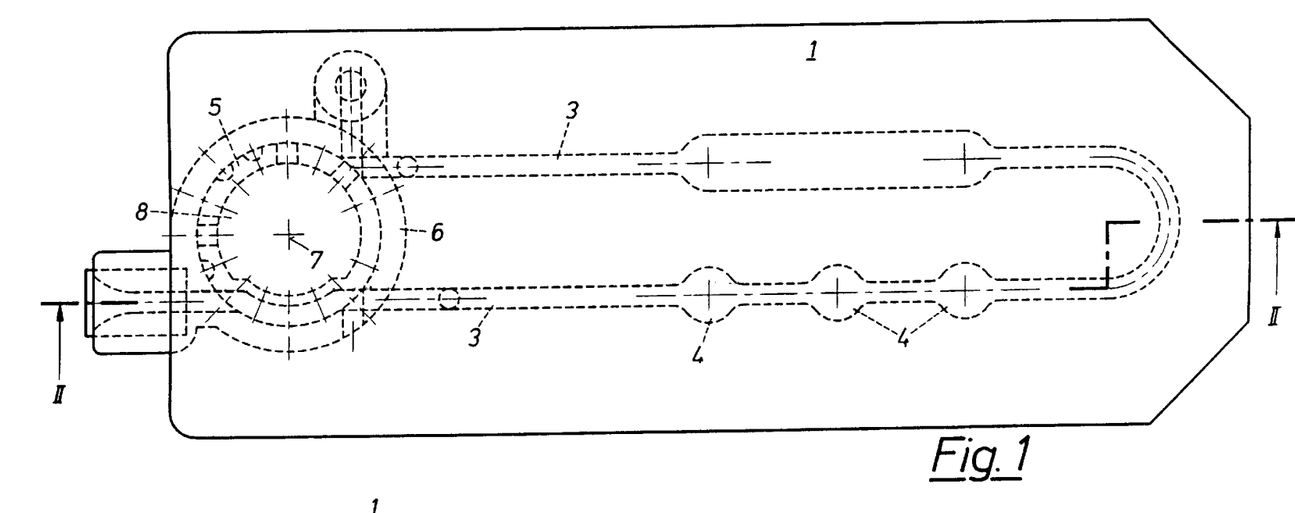
Figure 2:
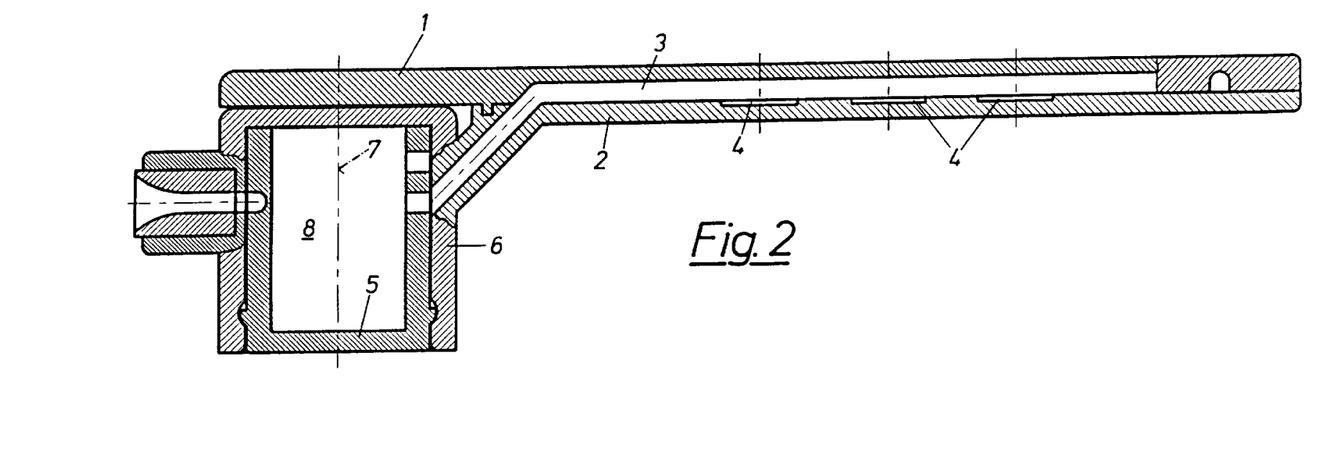

The cartridge substantially comprises an upper part 1 and a lower part 2 which are combined to form a U-shaped sample channel 3. The sample channel 3 contains sensors 4, for example, for measurement of pH, $CO_2$, $O_2$. For control of the different media a rotatable valve 5 is placed in a cup-shaped receptacle 6 moulded integral with the lower part 2, whose axis 7 is normal to the plane defined by the two legs of the sample channel 3. Inside the valve 5 configured as a hollow cylinder a waste container is provided to collect the conditioning liquids, calibrating media, quality control liquid, and the sample, if necessary. In the instance of dry-stored sensors the waste container 8 of the valve 5 may be used for storage of the calibrating liquid before the measuring process.

Suitable sensors for use with the method of the invention are optical or electrochemical sensors for pH, $pO_2$, $pCO_2$, $Li^+$, $Na^+$, $K^+$, $Mg^+$, $Ca^{++}$, $Cl^-$, glucose, lactate, urea (BUN), uric acid, creatinine, cholesterol.

As regards the composition of a conditioning liquid or a calibrating liquid for implementation of the method of quality control according to the invention, the following aspects should be considered;

If a pH measuring element is used: One-point calibration of pH measuring elements for biological fluids, such as whole blood, is conveniently performed at values in the physiologically normal pH range (7.35–7.45). To obtain these values, suitable chemical components of aqueous solutions are used, such as phosphates, organic zwitterionic compounds, e.g., HEPES, MOPS, TES (described in Good et al., Biochemistry 5, 467–477, 1996), and organic N-containing bases, such as TRIS.

Exemplary liquid: Water containing 0.008695 mol/kg KH2PO4 and 0.03043 mol/kg $Na_2PO_4$ in solubilized form, exhibits an ionic strength of 0.100 mol/kg and a pH of 7.385 at 37° C. in the absence of $CO_2$.

Adjustment of ionic strength: As the sensor characteristic of optical pH measuring elements in particular will depend on the ionic strength of liquid measuring media, the ionic strength of the conditioning or calibrating solution should be adjusted to the type of specimen being measured. Values of the ionic strength of whole blood are 0.130–0.170 mol/l, approximately.

For adjustment of the ionic strength salts which react neutral in aqueous solution may be added to the conditioning liquid or calibrating liquid. Suitable substances include all saline compounds of strong acids and strong bases that are soluble in aqueous environment, such as NaCl, KCl, LiCl, $Na_2SO_4$, $NaNO_3$, or salts of weak acids and weak bases (e.g., $CH_3COOLi$), if supplied in the interesting pH measuring range in dissociated or protonated form. Since such anions and cations could also be counterions of pH buffer components, the concentrations of all components must be adjusted correspondingly.

If pH and $CO_2$ measuring elements are used: For simultaneous one-point calibration of a $CO_2$ sensor provided in a single-use cartridge for blood gas analysis it will be an advantage if the liquid is subject to a $CO_2$ partial pressure in the physiologically normal range (35–45 torr, approx.). By application of 40 torr $CO_2$ the pH value referred to above will drop to 6.961 at an ionic strength of 0.092 mol/l. After the addition of 0.024 mol/l $NaHCO_3$ the pH will rise again to 7.385 at an ionic strength of 0.124 mol/l.

If $O_2$ measuring elements are used: For simultaneous one-point calibration of an $O_2$ sensor provided in a single-use cartridge it will be an advantage if the calibrating medium has a $pO_2$ in the physiologically normal range (90–110 torr, approx.). The ions of aqueous media usually have no influence on such sensors, whereas $pH_2O$ or osmotic pressure do influence them.

If ion sensors are used: For simultaneous one-point calibration of ion sensors additionally provided in a single-use cartridge (for example, for $Li^+$, $Na^+$, $K^+$, $Mg^{++}$, $Ca^{++}$, $Cl^-$) it will be a special advantage if the concentrations (or activities) of the respective cations and anions are adjusted to normal values of the specimen. Normal values of whole blood, for instance, are in the range of 135–150 mmol/l for $Na^+$, 3.5–5.0 mmol/l for $K^+$, 1.0–1.4 mmol/l for $Ca^{++}$, 98.0–119.0 mmol/l for $Cl^-$.

Exemplary Calibrating and Conditioning Media

If the single-use cartridge contains sensors for determination of pH, $pCO_2$ and $pO_2$, and the $K^+$, $Na^+$, and $Cl^-$ concentrations of whole blood, for example, an aqueous solution subject to 40 torr $CO_2$, 90 torr $O_2$ at 37° C., of the composition indicated below,

| Component | (mol/l) | Na+ (mol/l) | K+ (mol/l) | Cl− (mol/l) | ionic strength (mol/l) |
|---|---|---|---|---|---|
| NaH2PO4 | 0.0028 | 0.0028 | | | 0.0028 |
| Na2HPO4 | 0.0112 | 0.0224 | | | 0.0336 |
| NaHCO3 | 0.0243 | 0.0243 | | | 0.0243 |
| NaCl | 0.0960 | 0.0960 | | 0.0960 | 0.0960 |
| KCl | 0.0040 | | 0.0040 | 0.0040 | 0.0040 |
| Totals | | 0.1455 | 0.0040 | 0.1000 | 0.1607 | will fulfill the above requirements. The liquid has a pH of 7.385 (see FIG. 3, line X), ionic strength of 160 mmol/l, Na+ concentration of 145 mmol/l, $K^+$ concentration of 4 mmol/l, and $Cl^-$ concentration of 100 mmol/l.

Figure 3:
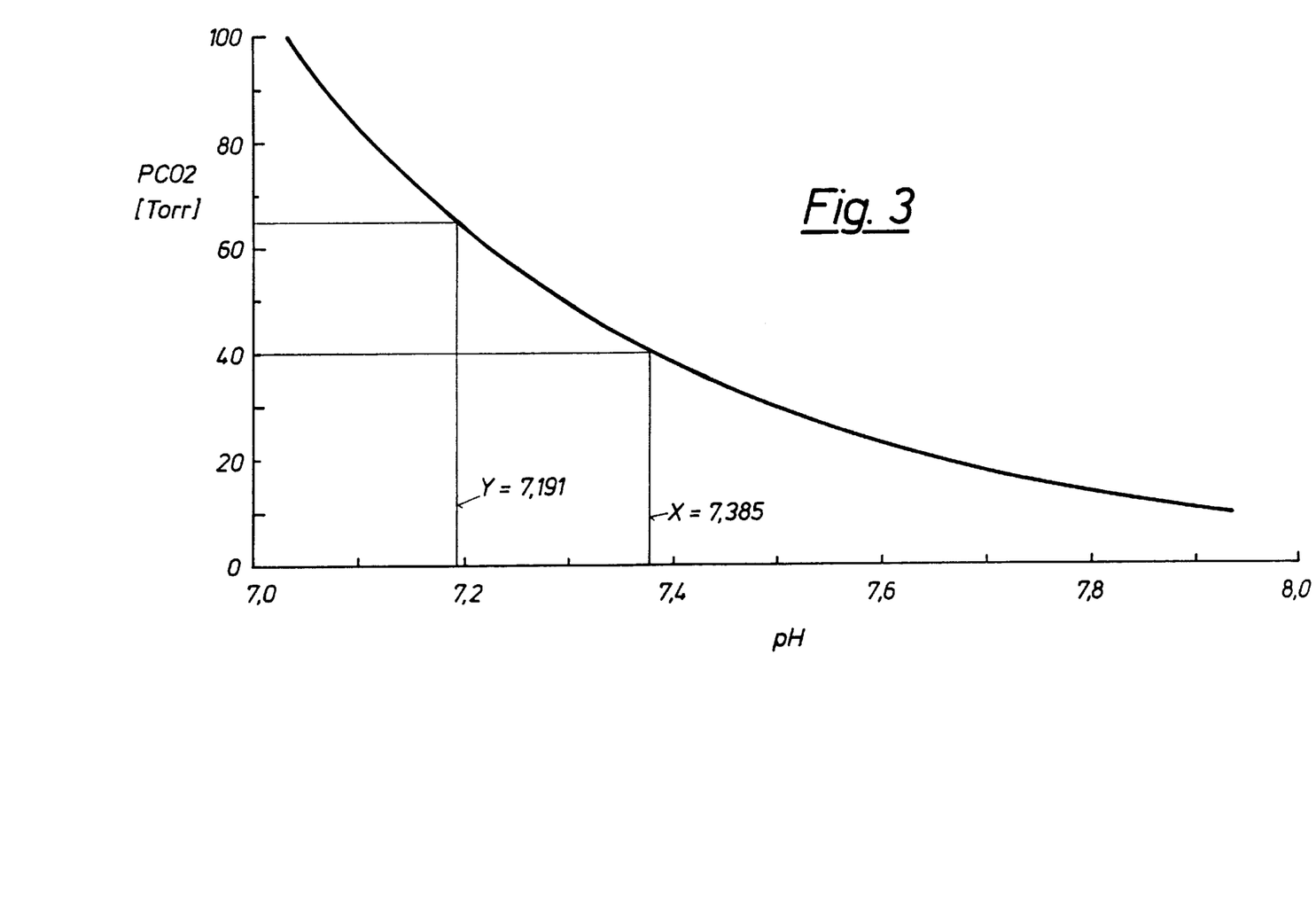
FIG. 3 depicts a $CO_2$/pH equilibrium curve for an embodiment of a calibrating and conditioning media for use in the cartridge of FIGS. 1 and 2.

The $CO_2$/pH equilibrium curve of this liquid is indicated in FIG. 3.

Tensides: Prolonged contact of the sensors with a conditioning liquid will lead to increased formation of bubbles. The presence of bubbles in the measuring device will make it more difficult to replace liquids by gaseous media. To avoid bubbling and improve wettability it is advantageous to add small quantities of tensides. (Examples: Triton X100: Du Pont Company, 549 Albany Str., Boston, Mass. 02118, USA; Dehydron 241, Dehydrol 100: Henkel Corporation, 300 Brookside Ave., Ambier, Pa. 19002, USA).

Biocides: Biological activities frequently lead to a change in the composition of aqueous solutions, in particular, a change in pH. Due to these activities pH is not known with sufficient accuracy at calibration or at the time of control measurement. For this reason it is recommended to add small quantities of biocides to the liquids. (Examples: $NaN_3$, Mergal K9N: manufactured by Riedel de Haan AG, marketed through Hoechst Austria AG, A-1121 Vienna, Austria; Proclin 300, Proclin 150: Supelco, Inc., Supelco Park, Bellefonte, Pa. 16823, USA; Bronidox L: Henkel Corporation, 1301 Jefferson Str., Hoboken, N.J. 07030, USA; Nuosept C: Huls America, Inc., Turner Place, P.O.Box 365, Piscataway, N.J. 08855).

Gas solubility: Further substances may be added to liquid calibrating media in order to increase gas solubility (for example, fluorocarbons for an increase of oxygen solubility).

Following is an example for the composition of a quality control liquid for implementation of the method according to the invention.

A suitable quality control liquid exhibits the parameters to be determined by means of the sensors in a single-use cartridge at concentrations or partial pressures identical with the respective expected values of the specimen. Preferably, the values of these parameters are identical with those of the calibrating liquid.

The control liquid is treated with a gas of known $O_2$ and $CO_2$ composition and is stored before use in a gas and water impermeable container (preferably a glass ampoule). The relative composition of the treated gaseous mixture may deviate from that of the conditioning or calibrating liquid.

The exemplary conditioning or calibrating liquid referred to above (see Table page 29) also is suited as quality control liquid. Since the quality control liquid is identical with the conditioning or calibrating liquid, all physical and chemical parameters will naturally be the same. It should be noted that a quality control liquid according to the invention need only be in accordance with those physical and/or chemical parameters which influence the sensor characteristic within the desired range of accuracy for the sample components to be measured.

It will thus suffice if the quality control liquid for use with the method of the invention is identical with the calibrating liquid and/or conditioning liquid as regards $CO_2$/pH equilibrium curve and ionic strength.

In the instance of sensors with ion-impermeable separating membranes, it is further recommended that the water vapor partial pressure of the control liquid be the same as that of the calibrating and/or conditioning liquid.

If further chemical additives are used the influences of their chemical parameters on the physical quantities referred to above must be taken into account.

With biological specimens (e.g., whole blood), in particular, it is often necessary to provide control values above and below the physiologically normal range of the respective measurement quantities, in addition to the control values inside this range.

For example, if the above quality control liquid is subject to 65 torr $CO_2$ and 60 torr $O_2$ at 37° C., the composition of the pH buffer components will change, while the concentrations of the cations and anions of saline compounds of strong acids with strong bases ($Na^+$, $K^+$, $Cl^-$) that are soluble in aqueous environment, will remain the same:

| Component | (mol/l) | Na+ (mol/l) | K+ (mol/l) | Cl− (mol/l) | ionic strength (mol/l) |
|---|---|---|---|---|---|
| NaH2PO4 | 0.0039 | 0.0039 | | | 0.0039 |
| Na2HPO4 | 0.0100 | 0.0200 | | | 0.0300 |
| NaHCO3 | 0.0255 | 0.0255 | | | 0.0255 |

-continued

| Component | (mol/l) | Na+ (mol/l) | K+ (mol/l) | Cl− (mol/l) | ionic strength (mol/l) |
|---|---|---|---|---|---|
| NaCl | 0.0960 | 0.0960 | | 0.0960 | 0.0960 |
| KCl | 0.0040 | | 0.0040 | 0.0040 | 0.0040 |
| Totals | | 0.1454 | 0.0040 | 0.1000 | 0.1594 |

The pH value is 7.191 (see FIG. 3, line Y). The $CO_2$/pH equilibrium curve remains the same. Within the desired measuring accuracy for the sample components to be measured the ionic strength will thus remain unchanged.

If additional control values for ion sensors are to be determined outside of the respective physiologically normal ranges, the concentrations of the neutral salts added may be modified. Since changes in the concentrations of the neutral salts will influence ionic strength, it is possible for the purpose of adjusting the ionic strength to that of the conditioning or calibrating liquid, to add yet another neutral salt whose anionic or cationic components differ from the sample parameters to be determined (e.g., $Li_2SO_4$, $LiNO_3$, $CH_3COOLi$).

| Component | (mol/l) | Na+ (mol/l) | K+ (mol/l) | Cl− (mol/l) | ionic strength (mol/l) |
|---|---|---|---|---|---|
| NaH2PO4 | 0.0039 | 0.0039 | | | 0.0039 |
| Na2HPO4 | 0.0100 | 0.0200 | | | 0.0300 |
| NaHCO3 | 0.0255 | 0.0255 | | | 0.0255 |
| NaCl | 0.0660 | 0.0660 | | 0.0660 | 0.0660 |
| KCl | 0.0060 | | 0.0060 | 0.0060 | 0.0060 |
| LiNO3 | 0.0280 | | | | 0.0280 |
| Totals | | 0.1154 | 0.0060 | 0.0720 | 0.1594 |

The liquid has a pH of 7.191. All exemplary sample parameters to be determined are outside of the physiologically normal range of whole blood. Nevertheless, $CO_2$/pH equilibrium curve and ionic strength remain unchanged (see FIG. 3, line Y).

The measuring process for use with wet-stored sensors (e.g., EP 0 460 343 B1) comprises the following steps:

Preparation of Cartridge & Conditioning

1. The sample chamber (sample channel) is filled once or repeatedly with conditioning liquid and closed afterwards.

2. The single-use cartridge is packaged in a gas and water impermeable container and stored until use. (Conditioning of the sensors may take place after filling of the measuring chamber or during storage).

3. The cartridge is removed from the package, the sensor characteristics are read into the measuring instrument, and the cartridge is inserted into the portable analyzer.

Calibration Measurement

4. The conditioning liquid in the sample chamber (sample channel) is displaced by a calibrating gas into a waste container (integrated in the cartridge, for example). Residues of the conditioning liquid will remain in the ion-permeable layers of the sensors and are subject to the calibrating gas together with the sensor materials.

5. The calibration signals of the different sensors are detected simultaneously.

Control Measurement

6. The calibrating gas is replaced by a quality control liquid according to the invention, which is supplied in a gas and water impermeable (glass) container.

7. The control signals of the different sensors are detected simultaneously.

8. The instantaneous control values (pH, concentrations/gas partial pressures) are determined, taking into account the sensor characteristics entered, the calibration signals detected (step 5) and the control signals detected (step 7). The instantaneous control values are subsequently displayed.

9. The instantaneous control values obtained in step 8 are compared with the known target control values, the differences in these values providing information on the accuracy and reliability of the portable analyzer, or rather, the cartridge.

Sample Measurement

10. The quality control liquid in the sample chamber (sample channel) is displaced by means of a calibrating gas into a waste container (integrated in the cartridge, for example).

11. The calibrating gas is replaced by the specimen (for example, blood).

12. The specimen signals of the different sensors are detected simultaneously.

13. The measurement variables (pH, concentrations/gas partial pressures) are determined, taking into account the sensor characteristics entered, the calibration signals detected (step 5), and the specimen signals detected (step 12). The measured quantities are subsequently displayed.

The measuring process for use with dry-stored sensors (e.g., WO 92/01928) comprises the following steps:

Preparation of Cartridge

1. A gas and water impermeable reservoir preferably contained in the single-use cartridge is filled with calibrating liquid and closed afterwards.

2. The cartridge is packaged in a gas and water impermeable container and stored until use.

3. The cartridge is removed from the package, the sensor characteristics are read into the measuring instrument, and the cartridge is inserted into the portable analyzer.

Calibration Measurement

4. A connection is established between the reservoir and the sample chamber (sample channel). The calibrating liquid in the reservoir is transferred into the sample chamber (sample channel).

5. The calibration signals of the different sensors are detected simultaneously, taking into account the time of signal detection relative to the time of primary contact with the calibrating liquid.

Control Measurement

6. The calibrating liquid in the sample chamber (sample channel) is replaced by a gaseous medium of known composition (ambient air, among others). The gaseous medium in the sample chamber (sample channel) is replaced by a quality control liquid according to the invention, which is supplied in a gas and water impermeable (glass) container.

7. The control signals of the different sensors are detected simultaneously, taking into account the time of signal detection relative to the time of primary contact with the calibrating liquid.

8. The instantaneous control values (pH, concentrations/gas partial pressures) are determined, taking into account the sensor characteristics entered, the time of detection of the specimen signals relative to the time of primary contact with the calibrating liquid, the calibration signals detected (step 5) and the control signals detected (step 7).

9. The instantaneous control values obtained in step 8 are compared with the known target control values, the differences in these values providing information on the accuracy and reliability of the portable analyzer, or rather, the cartridge.

Sample Measurement

10. The quality control liquid in the sample chamber (sample channel) is replaced by a gaseous medium of known composition (ambient air, for example), and transferred into a waste container (integrated in the cartridge, for example).

11. The gaseous medium in the sample chamber (sample channel) is replaced by the specimen (for example, blood).

12. The specimen signals of the different sensors are detected simultaneously, taking into account the time of signal detection relative to the time of primary contact with the calibrating liquid.

13. The measurement variables (pH, concentrations/gas partial pressures) are detected and displayed, taking into account the sensor characteristics entered, the time of specimen signal detection relative to the time of primary contact with the calibrating liquid, the calibration signals detected (step 5), and the specimen signals detected (step 12). The measured quantities are subsequently displayed.

We claim:

1. Method for quality control of an analyzing system consisting of a portable analyzer with insertable single-use cartridges whose sample chamber contains at least one optical and/or electrochemical ion sensor selected from the group consisting of pH, $Li^+$, $K^+$, $Na^+$, $Mg^{++}$, $Ca^{++}$ and $Cl^-$ sensors and at least one optical and/or electrochemical gas sensor selected from the group consisting of $O_2$ and $CO_2$ sensors, wherein said sensors are stored in contact with a conditioning liquid, comprising the steps of:

a) reading production-inherent characteristics of the individual ion and gas sensors into the analyzer, or using already stored characteristics, and inserting the cartridge into the analyzer;

b) replacing the conditioning liquid present in the sample chamber by a gaseous calibrating medium, wherein residues of the conditioning liquid remaining in ion-permeable layers of the ion sensors are treated with the gaseous calibrating medium to thereby form a calibrating liquid, and wherein the gaseous calibrating medium contacts the gas sensors;

c) simultaneously detecting calibration signals of the ion and gas sensors;

d) contacting the ion and gas sensors with a quality control liquid, which, as regards those chemical and/or physical parameters that influence the characteristic of at least one ion or gas sensor during calibration or conditioning, is identical with the conditioning liquid within a predetermined range of accuracy for the sample components to be measured;

e) simultaneously detecting control signals of the sensors;

f) determining instantaneous control values for the individual sensors with the use of the characteristics entered or stored in the analyzer and the calibration and control signals detected in steps c) and e);

g) comparing the instantaneous control values with known target control values; and h) subsequent to the process of quality control, employing the same cartridge for sample measurement, if the instantaneous control values are identical with the target control values within the predetermined range of accuracy.

2. Method according to claim 1, wherein in step d) the sensors are contacted immediately prior to sample measurement with a quality control liquid whose $CO_2$/pH equilibrium curve and $pH_2O$ in a measuring range and at a given measuring temperature are identical with the respective values of the conditioning liquid within the predetermined range of accuracy for the sample components to be measured.

3. Method according to claim 2, wherein the ionic strength of the quality control liquid is identical with that of the conditioning liquid in the measuring range and at a given pH, within the predetermined range of accuracy for the sample components to be measured.

4. Method according to claim 2, wherein the osmotic pressure of the quality control liquid is identical with that of the conditioning liquid within the predetermined range of accuracy for the sample components to be measured.

5. Method for quality control of an analyzing system consisting of a portable analyzer with insertable single-use cartridges whose sample chamber contains at least one optical and/or electrochemical ion sensor selected from the group consisting of pH, $Li^+$, $K^+$, $Na^+$, $Mg^{++}$, $Ca^{++}$ and $Cl^-$ sensors, wherein said sensors are stored in contact with a conditioning liquid, comprising the steps of:

a) reading production-inherent characteristics of the individual ion sensors into the analyzer, or using already stored characteristics, and inserting the cartridge into the analyzer;

b) replacing the conditioning liquid present in the sample chamber by a gaseous calibrating medium, wherein any residues of the conditioning liquid remaining in ion-permeable layers of the ion sensors are treated with the gaseous calibrating medium to form a calibrating liquid;

c) simultaneously detecting calibration signals of the ion sensors;

d) contacting the ion sensors with a quality control liquid, which, as regards those chemical and/or physical parameters that influence the characteristic of at least one sensor during calibration or conditioning, is identical with the conditioning liquid within a predetermined range of accuracy for the sample components to be measured;

e) simultaneously detecting control signals of the sensors;

f) determining instantaneous control values for the individual sensors with the use of the characteristics entered or stored in the analyzer and the calibration and control signals detected in steps c) and e);

g) comparing the instantaneous control values with known target control values; and h) subsequent to the process of quality control, employing the same cartridge for sample measurement, if the instantaneous control values are identical with the target control values within the predetermined range of accuracy.

6. Method according to claim 5, wherein in step d) the sensors are contacted immediately prior to sample measurement with a quality control liquid whose $CO_2$/pH equilibrium curve and $pH_2O$ in a measuring range and at a given measuring temperature are identical with the respective values of the conditioning liquid within the predetermined range of accuracy for the sample components to be measured.

7. Method according to claim 6, wherein the ionic strength of the quality control liquid is identical with that of the conditioning liquid in a predetermined measuring range and at a given pH, within the predetermined range of accuracy for the sample components to be measured.

8. Method for quality control of an analyzing system consisting of a portable analyzer with insertable single-use cartridges whose sample chamber contains optical and/or electrochemical sensors, wherein said sensors are dry-stored comprising the steps of:

a) reading production-inherent characteristics of the individual sensors into the analyzer, or using already stored characteristics, and inserting the cartridge into the analyzer;

b) subjecting the sensors to a calibrating liquid;

c) simultaneously detecting calibration signals of the sensors, taking into account the time lapse between the primary contact of the sensors and the calibrating liquid and the detection of the calibration signals;

d) contacting the sensors with a quality control liquid, which, as regards those chemical and/or physical parameters that influence the characteristic of at least one sensor during calibration, is identical with the calibrating liquid within a predetermined range of accuracy for sample components to be measured;

e) simultaneously detecting control signals of the sensors taking into account the time lapse between the primary contact of the sensors and the calibrating liquid and the detection of the control signals;

f) determining instantaneous control values for the individual sensors from the characteristics entered or stored in the analyzer, and the calibration and control signals detected in steps c) and e);

g) comparing the instantaneous control values with known target control values; and h) subsequent to the process of quality control, employing the same cartridge for sample measurement, if the instantaneous control values are identical with the target control values within the predetermined range of accuracy.

9. Method according to claim 8, wherein in step d) the sensors are contacted immediately prior to sample measurement with a quality control liquid whose $CO_2$/pH equilibrium curve and $pH_2O$ in a measuring range and at a given measuring temperature are identical with the respective values of the calibrating liquid of step b) within the predetermined range of accuracy for the sample components to be measured.

10. Method according to claim 9, wherein the ionic strength of the quality control liquid is identical with that of the calibrating liquid in the measuring range and at a given pH, within the predetermined range of accuracy for the sample components to be measured.

11. Method according to claim 9, wherein the osmotic pressure of the quality control liquid is identical with that of the calibrating liquid within the predetermined range of accuracy for the sample components to be measured.

12. Method according to claim 8, wherein in step d) a gas of known composition for the purpose of separating the calibrating liquid from the quality control liquid is added.

* * * * *

UNITED STATES PATENT AND TRADEMARK OFFICE
CERTIFICATE OF CORRECTION

PATENT NO. : 6,037,178
DATED : March 14, 2000
INVENTOR(S) : Marco Jean-Pierre LEINER et al.

It is certified that error appears in the above-identified patent and that said Letters Patent is hereby corrected as shown below:

On the title page item [75] inventors: Marco Jean-Pierre LEINER, Graz, Austria; James K. Tusa, Alpharetta, Ga.

Signed and Sealed this

Sixth Day of February, 2001

*Attest:*

Q. TODD DICKINSON

*Attesting Officer*  *Director of Patents and Trademarks*